United States Patent [19]

Kalender et al.

[11] 4,324,978
[45] Apr. 13, 1982

[54] TOMOGRAPHIC X-RAY APPARATUS FOR THE PRODUCTION OF TRANSVERSE LAYER IMAGES

[75] Inventors: Willi Kalender; Gerhard Linke; Manfred Pfeiler, all of Erlangen, Fed. Rep. of Germany

[73] Assignee: Siemens Aktiengesellschaft, Berlin & Munich, Fed. Rep. of Germany

[21] Appl. No.: 156,407

[22] Filed: Jun. 4, 1980

[30] Foreign Application Priority Data

Jul. 17, 1979 [DE] Fed. Rep. of Germany ....... 2928825

[51] Int. Cl.³ .............................................. A61B 6/00
[52] U.S. Cl. ................................................. 250/445 T
[58] Field of Search ................................... 250/445 T

[56] References Cited

U.S. PATENT DOCUMENTS

| 4,118,631 | 10/1978 | Froggatt | 250/445 T |
| 4,150,293 | 4/1979 | Franke | 250/445 T |
| 4,174,481 | 11/1979 | Liebetruth | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, the measuring arrangement including the x-ray tube and radiation receiver, is capable of being locked against rotation, and the patient support is capable of being locked against longitudinal movement. The x-ray beam is selectively limited in extent by means of an adjustable diaphragm. In the case of a locked measuring arrangement and patient support and a limited x-ray beam, the measured values of the radiation receiver are detected by a computer which, from them and from information regarding the cross section of a vessel to be examined, determines the concentration and/or quantity of an x-ray contrast agent therein. The information regarding the cross section is obtained with a normal computer tomographic scanning operation.

2 Claims, 1 Drawing Figure

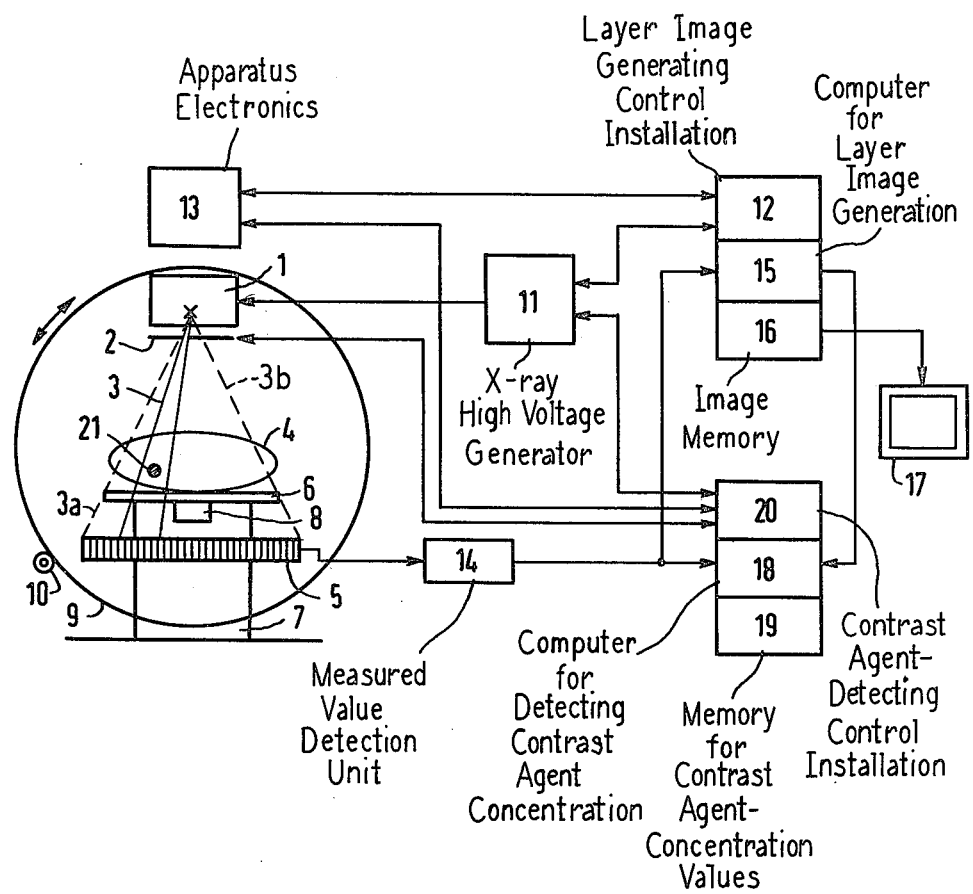

TOMOGRAPHIC X-RAY APPARATUS FOR THE PRODUCTION OF TRANSVERSE LAYER IMAGES

BACKGROUND OF THE INVENTION

The invention relates to a tomographic x-ray apparatus for the production of transverse layer images of a radiography subject, comprising a patient support, a radiation measuring arrangement with an x-ray source which generates a beam of rays penetrating the radiography subject and whose cross-sectional extent perpendicular to the layer plane is equal to the layer thickness, and a radiation receiver which determines the radiation intensity behind the subject, comprising a driving device coupled with the measuring arrangement for effecting rotational movement thereof, comprising a measured value converter for conversion of the signals supplied by the radiation receiver into a layer image, and comprising means for locking the measuring arrangement against rotation during the processing of the measuring signals delivered by the radiation receiver.

For the production of transverse layer images, computer aided tomographic apparatus is known which exhibits a radiation measuring arrangement with which the transverse layer is scanned from different projections. From the output signals of the radiation receiver of the radiation measuring arrangement a computer calculates the image of the examined transverse layer.

In the case of specific x-ray-diagnostic examinations accompanied by the use of contrast agents, the physician requires quantitative information regarding the contrast agent concentration and its chronological travel path (or course, or progression), for example in larger blood vessels.

SUMMARY OF THE INVENTION

The object underlying the invention resides in designing a computer aided tomographic apparatus such that with the latter an examination of the contrast agent concentration and its chronological travel path (or progression) in a vessel or in the organ tissue is possible.

In solving this problem one proceeds from an x-ray tomographic apparatus of the type initially cited, such as is described in the German Auslegeschrift No. 26 13 809. In the case of this known computer tomograph it is possible to lock the measuring arrangement against rotation during the processing of the output signals of the radiation receiver. This locking, however, has the purpose, with the aid of a longitudinal movement of the patient support, of producing an x-ray shadow image. The travel path (or course, or progression) of a contrast agent at a specified location of the examined layer is thus not detectable.

The object underlying the invention is solved in accordance with the invention in that means for locking the patient support against longitudinal movement during the processing of the measuring signals are present, and that an adjustable diaphragm for limiting (or localizing) the beam of rays to a segment of the layer plane is provided. In the case of the inventive tomographic x-ray apparatus the measuring arrangement as well as the patient support can be locked during the processing of the measuring signals. It is therefore possible to precisely trace the travel path (or course, or progression) of the contrast agent at a specified location which is restricted in comparison to a complete layer cross section. The beam of x-rays can be bounded (or restricted) by means of an adjustable diaphragm, which corresponds to the desired layer segment to be examined. The radiation exposure on the part of the patient is therefore extremely low.

A particularly advantageous embodiment is one wherein the radiation receiver comprises a series of detector elements and has such a dimension that, with complete irradiation, it detects the cross-section of a patient of which an image is to be formed, and that through the beam restricting diaphragm a portion only of the detector elements is selectable. With this design all detector elements can be selectively utilized for the production of a conventional computer tomography image, whereas only the respectively required detector elements are utilized for tracing the progress of the contrast agent.

The invention shall be explained in greater detail below on the basis of an exemplary embodiment as illustrated on the accompanying drawing sheet; and other objects, features and advantages will be apparent from this detailed disclosure and from the appended claims.

BRIEF DESCRIPTION OF THE DRAWING

The single FIGURE includes a diagrammatic transverse view of a computer assisted x-ray tomographic apparatus and shows also a block circuit diagram for indicated associated electric circuitry, the illustrated apparatus and circuitry including modifications and additions for disclosing an embodiment in accordance with the teachings and concepts of the present invention.

DETAILED DESCRIPTION

In the drawing an x-ray tube 1 is illustrated which generates an x-ray beam 3, bounded or delimited by means of a diaphragm 2, which x-ray beam penetrates a patient 4 in a segment of a transverse layer. The dimension of the x-ray beam 3 perpendicular to the layer plane is equal to the layer thickness. The x-radiation issuing (or emerging) from the patient 4 impinges upon a radiation receiver 5 which consists of a series of detector elements and has such a dimension that, with complete irradiation; i.e., with a completely opened diaphragm 2, it detects transmitted radiation over the entire cross-section of the patient 4 of which an image is to be made. The x-ray beam is illustrated in broken lines for this instance and marginal rays are referenced with 3a and 3b.

The patient 4 rests on a patient support 6 which is connected to a base (or pedestal) 7 and which can be locked against longitudinal movement by means of a locking device 8. The measuring arrangement, consisting of the x-ray tube 1 and the radiation receiver 5, is arranged on a schematically illustrated rotating ring 9 which can be rotated by a drive 10 in a rotational direction as indicated by the arrow for the purpose of scanning the patient 4 from different projections. The drive 10 can lock the rotating ring 9 and hence the measuring arrangement 1, 5, in a specified projection.

The x-ray tube 1 is fed by an x-ray high voltage generator 11 which is connected to a control installation 12 which also controls apparatus electronics 13. The radiation receiver 5 is connected to a measured value detection unit 14 which activates a computer 15 which calculates, from the data supplied by the measured value detection unit 14, an image of the examined transverse layer of the patient 4. The computed image can be stored in an image memory 16 and optically reproduced on a display unit 17. The measuring data of the measured value detection unit 14 are obtained for the purpose of image reconstruction, during the rotation of the measuring arrangement 1, 5 through an angle of 360° about the patient 4 from different projections.

The measured value detection unit 14 is connected to an additional computer 18 which serves for the determination of the contrast agent concentration in a specified area e.g. 21 of the examined transverse layer. The values determined by the computer 18 can be stored in a memory 19. It cooperates with a control installation 20.

For the determination of the contrast agent concentration, first a conventional scanning of the patient 4 is carried out and, by means of the computer 15, an image of the examined transverse layer is determined. Thus, for example, the cross section of a blood vessel, in which the contrast agent concentration is to be determined, can be calculated. Corresponding information regarding this cross section is provided by the computer 15 to the computer 18. Subsequently, the x-ray beam, which originally impinged on the entire radiation receiver 5 for the purpose of image production, is bounded or restricted from its size with marginal rays 3a, 3b to the size 3 by means of the diaphragm 2. The diaphragm adjustment proceeds from the control installation 20, corresponding to the portion of the radiation receiver 5, input by the user, which is intended to measure the x-radiation. Thus, it permeates (or traverses) the transverse layer of the patient 4 only in the area of a blood vessel 21. In addition, by means of the drive device 10, the rotating ring 9 is locked against rotation, and the patient support 6 is locked against longitudinal movement by means of the locking device 8. In the case of a stationary patient 4 and a stationary measuring arrangement 1, 5, the measured values of those detectors, which are impinged on by the x-ray beam 3 issuing (or emerging) from the patient 4, are detected by means of the measured value detection unit 14 and supplied to the computer 18. The computer 18 can determine the contrast agent concentration from the measured values and the information regarding the cross section of the vessel 21. In addition it is possible in this fashion to ascertain (or determine) the quantity of contrast agent. The data ascertained by the computer 18 can be reproduced e.g. on a viewing screen graphically as well as in the form of numerical values.

In addition to the diaphragm 2 a corresponding diaphragm can also be arranged between the patient 4 and the radiation receiver 5.

It will be apparent that many modifications and variations may be effected without departing from the scope of the novel concepts and teachings of the present invention.

SUPPLEMENTARY DISCUSSION

By way of background, the disclosure of U.S. Pat. No. 4,174,481 issued Nov. 13, 1979 is incorporated herein by reference, said patent corresponding to German Auslegeschrift No. 26 13 809, and being assigned to the assignee of the present application. Said patent (at columns 5 and 6) describes an exemplary radiation receiver which is disclosed in further detail in a U.S. application Ser. No. 940,562 filed Sept. 8, 1978, assigned to the assignee of the present application and identified by assignee reference number VPA 76 P 5058. U.S. Pat. No. 4,135,247 issued Jan. 16, 1979, and assigned to the assignee of the present application and identified by assignee reference number VPA 77 P 8907, shows in a fourth figure a multiplexing and analog to digital conversion circuit which may be embodied in measured value detection unit 14 herein.

By way of example, the control installation 20 may have a switch for activating the contrast agent detection mode. The control installation 20 may further be provided with selective switching means for selecting desired outputs from the detection unit 14. As disclosed in the aforementioned U.S. Pat. No. 4,135,247, component 14 may include a reset integrator circuit for each detector of receiver 5, and there may be a total of two hundred and fifty-six detectors whose integrated output signals may be scanned by a multiplex circuit and converted to digital form, in unit 14. The multiplex circuit of unit 14 may have a series of two hundred and fifty-six multiplex conditions which may be assigned addresses corresponding to decimal numbers one through two hundred and fifty-six. During tomography mode the addresses may be sequentially scanned by means of a binary counter and decoder, for example, in step with the addressing of memory locations for computer 15. In the contrast agent detection mode, the output of the detection unit 14 is connected to computer 18 instead of computer 15. The control installation 20 may include an address counter which is stepped through 256 count conditions in synchronism with the multiplex addressing in the multiplexer of component 14. The control installation 20 may further include address register and comparator circuits for registering in coded digital form values corresponding to the addresses of the detectors of receiver 5 whose outputs are to be stored in computer 18. For example, if detectors with multiplex addresses of decimal twenty-one, twenty-two and twenty-three were aligned with the radiation beam segment 3 of interest then a keyboard of unit 20 which is coupled with computer 18 could be utilized to load the first-scanned multiplex address, e.g. twenty-one, into an A address register and comparator of installation 20. The computer 18 could also be advised that the outputs from two further detectors in the scanning sequence after number twenty-one, were also to be stored, for example the computer 18 then loading into a B register and comparator circuit of component 20 the last to be scanned multiplex address of interest, e.g. twenty-three.

The loading of the detector selection information into the A and B registers of control installation 20 during contrast agent detecting mode could result in corresponding automatic positioning of A and B parts of diaphragm 2. Thus the A diaphragm part would be automatically positioned under the control of the A register so that detectors one through twenty were shielded from radiation, while the B diaphragm part would be automatically positioned under the control of the B register so that detectors twenty-four through two hundred and fifty-six were shielded from radiation.

The control installation could further include a timer for setting the frequency and total number of exposures desired during a contrast agent detection operation. Then upon actuation of a start switch, the timer would cause pulses of x-ray energy at the desired time interval. Each such pulse would result in integrated output signals from the integrators associated with detectors number twenty-one through twenty-three. At the end of each x-ray pulse, the address circuit controlling multiplexing within component 14 would be stepped through the read-in cycle and at the same time the corresponding address counter of control installation 20 would be cycled in step with the multiplex addressing of unit 14. At a count of decimal twenty-one, the computer 18 would be notified by means of the A register and comparator of installation 20 to begin storing values from unit 14. Such storage of values would be terminated after reading of the value identified by the B register and comparator of installation 20. Each time the timer of installation 20 caused generator 11 to produce a further pulse of x-ray energy, the computer 18 would store the resultant set of readings. The computer 18 could store with each set of readings an elapsed time reading from the timer of installation 20, if desired. At the completion of the constant agent detection operation, therefore, computer 18 would have stored a desired number of sets of readings from which the concentration of contrast agent at the location 21 as a function of time could be computed.

Where the actual multiplex circuit of unit 14 is operable via first and second levels as in U.S. Pat. No. 4,135,247, it will be apparent that a manual selector of component 20 can instruct the computer 18 to store the relevant multiplex addresses designated as in the previous example, the computer translating the serial number identification (i.e. no. 1 through no. 256) into the corresponding set of multiplex address slots, so that the computer itself can identify, among the stream of data (including undesired total absorption values) from the unit 14, the relevant values corresponding to the selected beam segment 3. The input by the manual selector of component 20 can again load A and B registers of component 20 for correspondingly positioning the A and B parts of diaphragm 2 as previously described (based on the straightforward serial number identification of detectors).

We claim as our invention:

1. Tomographic x-ray apparatus for the production of transverse layer images of a radiography subject, comprising a patient support, a radiation measuring arrangement including a radiation source which generates a beam of rays penetrating the radiography subject, whose cross sectional extent perpendicular to the layer plane is equal to the layer thickness, and a radiation receiver which determines the radiation intensity behind the subject, comprising a drive device for the measuring arrangement for producing rotational movement of the radiation measuring arrangement, and comprising a measured value converter for the conversion of the signals supplied by the radiation receiver into a tomographic image, means (10) for locking the measuring arrangement against rotation during the processing of the measuring signals supplied by the radiation receiver, means (8) for locking the patient support (6) against longitudinal movement during the processing of the measuring signals, and an adjustable diaphragm (2) for restricting the beam of rays (3) to a selected portion of the layer plane.

2. Tomographic x-ray apparatus according to claim 1, said adjustable diaphragm (2) in one condition thereof providing for irradiation by said radiation source of a complete cross section of a patient (4), and characterized in the radiation receiver (5) comprising a series of detector elements of such a dimension that in said one condition of said adjustable diaphragm the radiation receiver detects such a complete cross section of a patient (4), of which an image can be formed, and selecting means (20) for selecting a condition of the diaphragm (2) to restrict the beam to a selected portion (21) of the complete patient cross section.

* * * * *